United States Patent
Akagane

(10) Patent No.: US 9,764,165 B2
(45) Date of Patent: Sep. 19, 2017

(54) ULTRASONIC TRANSMITTING UNIT

(71) Applicant: OLYMPUS CORPORATION, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 408 days.

(21) Appl. No.: 14/460,057

(22) Filed: Aug. 14, 2014

(65) Prior Publication Data

US 2015/0057577 A1    Feb. 26, 2015

Related U.S. Application Data

(63) Continuation of application No. PCT/JP2013/067893, filed on Jun. 28, 2013.
(Continued)

(51) Int. Cl.
   *B06B 3/00*      (2006.01)
   *A61N 7/00*      (2006.01)
   (Continued)

(52) U.S. Cl.
   CPC ........ *A61N 7/00* (2013.01); *A61B 17/320068* (2013.01); *A61B 2017/22015* (2013.01); *A61N 2007/0043* (2013.01)

(58) Field of Classification Search
   CPC .............. A61N 7/00; A61N 2007/0043; A61B 17/320068; A61B 2017/22015
   See application file for complete search history.

(56) References Cited

U.S. PATENT DOCUMENTS 2,948,154 A * 8/1960 Kleesattel ................ A61C 1/07
                                                    367/152
2,960,314 A * 11/1960 Bodine, Jr. ............. B06B 1/186
                                                    116/137 A
(Continued)

FOREIGN PATENT DOCUMENTS

JP    A-63-302842    12/1988
JP    A-02-229584     9/1990
(Continued)

OTHER PUBLICATIONS

Mar. 19, 2015 International Preliminary Report on Patentability issued in International Application No. PCT/JP2013/067893.
(Continued)

*Primary Examiner* — Zakaria Elahmadi
(74) *Attorney, Agent, or Firm* — Oliff PLC

(57) ABSTRACT

An ultrasonic transmitting unit includes a first vibrating section and a second vibrating section vibrating at the same predetermined frequency with respect to each other. The ultrasonic transmitting unit includes a relay portion transmitting an ultrasonic vibration from the first vibrating section to the second vibrating section and positioned at a position corresponding to one of an antinode position of the vibration in the first vibrating section and a position different from an antinode position and a node position of the vibration in the second vibrating section, and a non-contact vibrating portion extending in the second vibrating section from the relay portion toward a first vibrating section side with being not in contact with the first vibrating section.

13 Claims, 12 Drawing Sheets

Related U.S. Application Data

(60) Provisional application No. 61/697,074, filed on Sep. 5, 2012.

(51) Int. Cl.
*A61B 17/32* (2006.01)
*A61B 17/22* (2006.01)

(56) References Cited

U.S. PATENT DOCUMENTS

| | | | | |
|---|---|---|---|---|
| 3,017,792 A | * | 1/1962 | Elmore | B06B 3/00 228/1.1 |
| 4,281,987 A | * | 8/1981 | Kleesattel | A61C 1/07 15/22.1 |
| 4,490,114 A | * | 12/1984 | Kleesattel | A61C 17/005 433/105 |
| 4,620,121 A | * | 10/1986 | Mishiro | B06B 3/00 310/323.18 |
| 4,799,622 A | * | 1/1989 | Ishikawa | B05B 17/0623 239/102.2 |
| 5,312,329 A | * | 5/1994 | Beaty | A61B 17/320068 604/22 |
| 2002/0170357 A1 | * | 11/2002 | Giordano | A61B 17/320068 73/570 |
| 2004/0047485 A1 | | 3/2004 | Sherrit et al. | |
| 2009/0143796 A1 | * | 6/2009 | Stulen | A61B 17/320068 606/169 |
| 2012/0169185 A1 | * | 7/2012 | Harris | H01L 41/047 310/365 |

FOREIGN PATENT DOCUMENTS

| | | |
|---|---|---|
| JP | A-2000-506431 | 5/2000 |
| JP | A-2000-515059 | 11/2000 |
| JP | A-2002-58679 | 2/2002 |
| JP | A-2010-535089 | 11/2010 |

OTHER PUBLICATIONS

International Search Report issued in International Patent Application No. PCT/JP2013/067893 dated Sep. 24, 2013.
Apr. 12, 2016 Extended European Search Report issued in European Application No. 13834428.8.

* cited by examiner

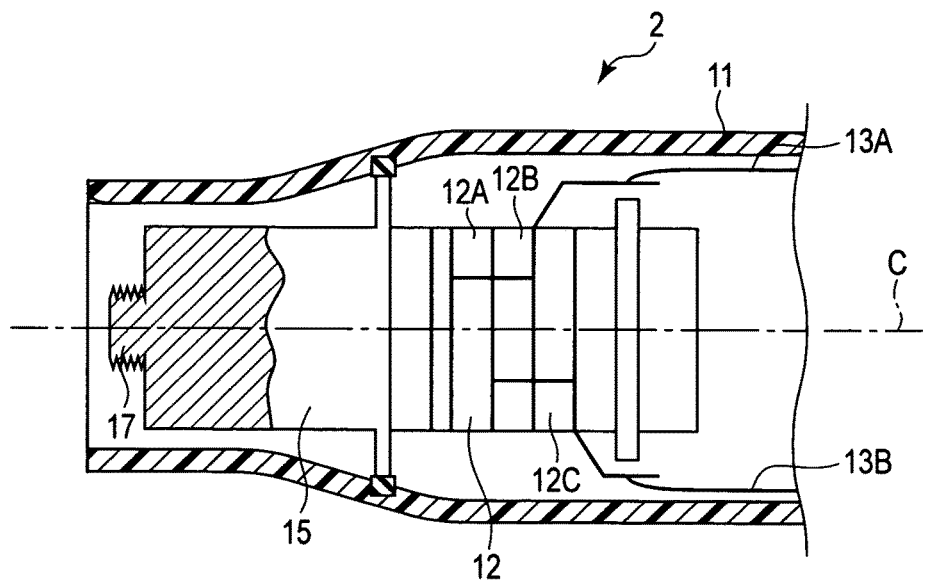
F I G. 2
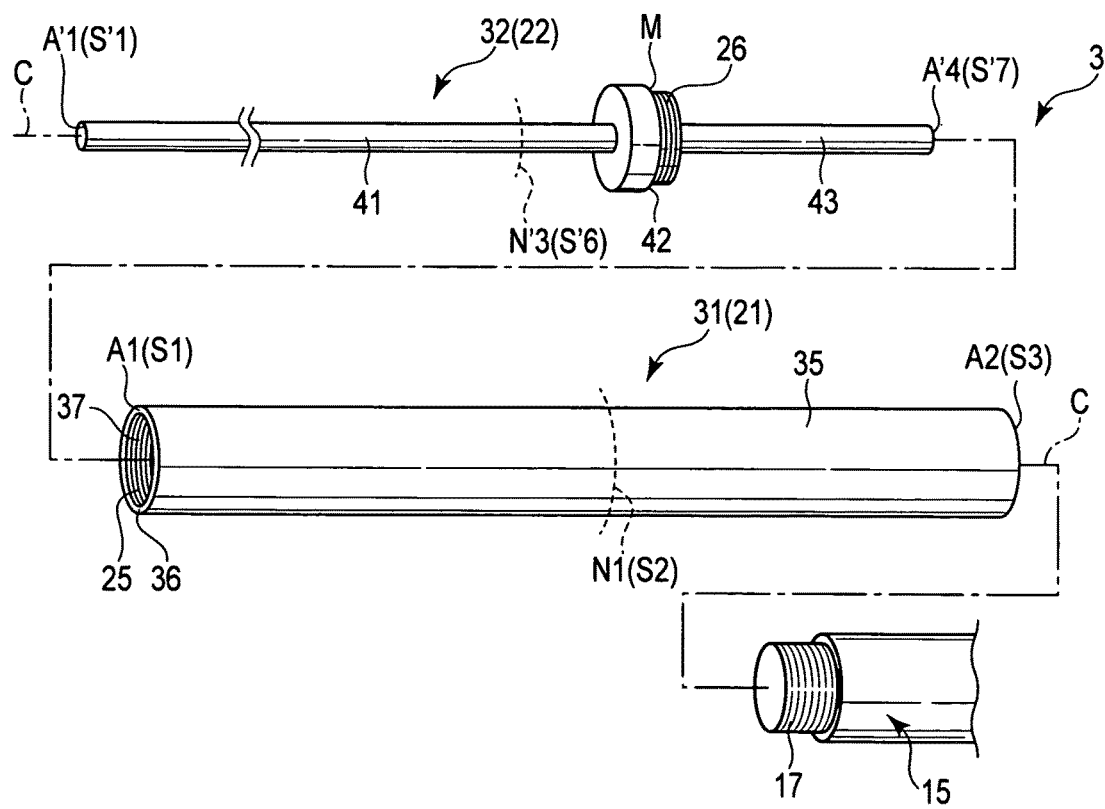
F I G. 3

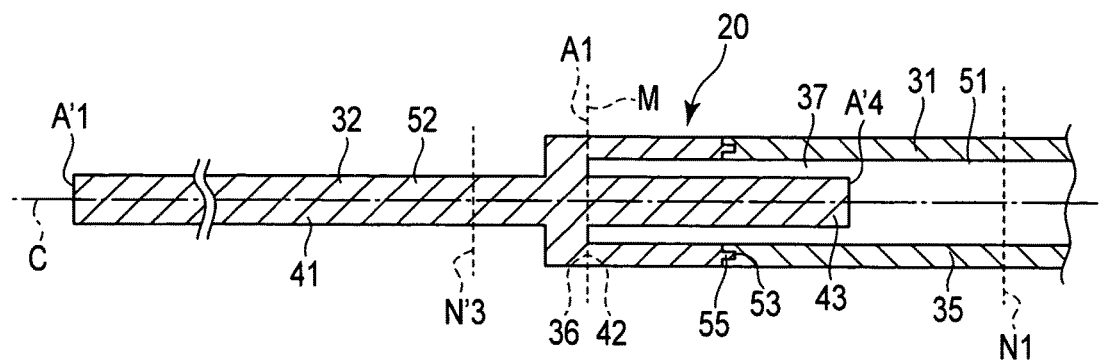
F I G. 16
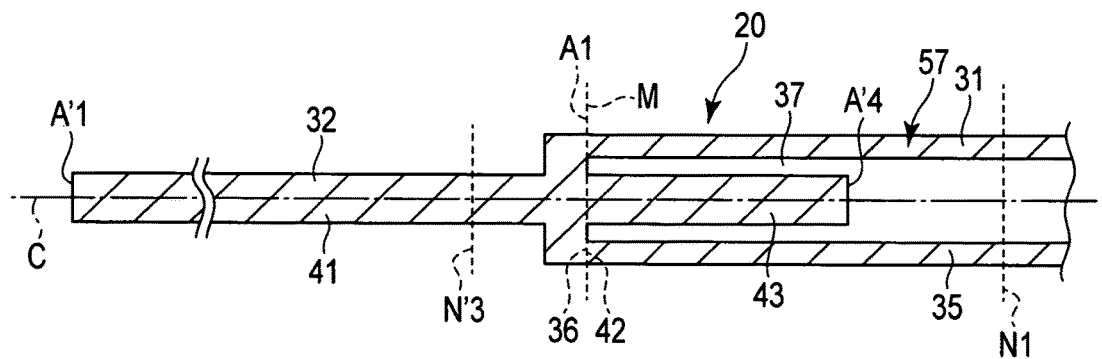
F I G. 17
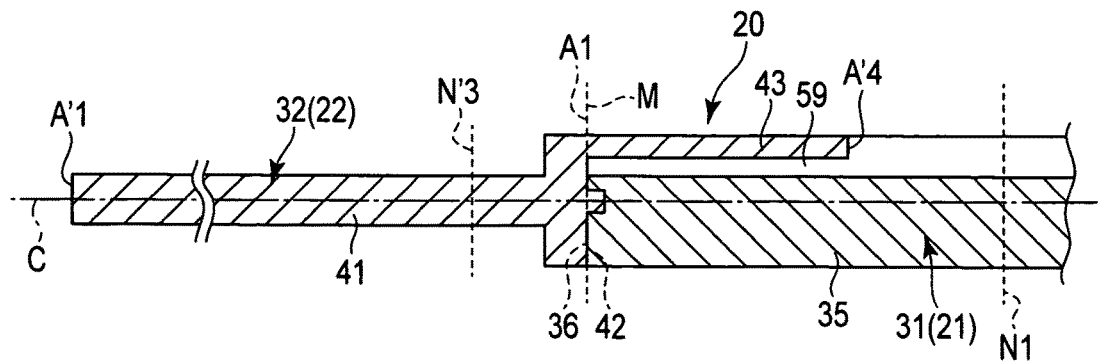
F I G. 18

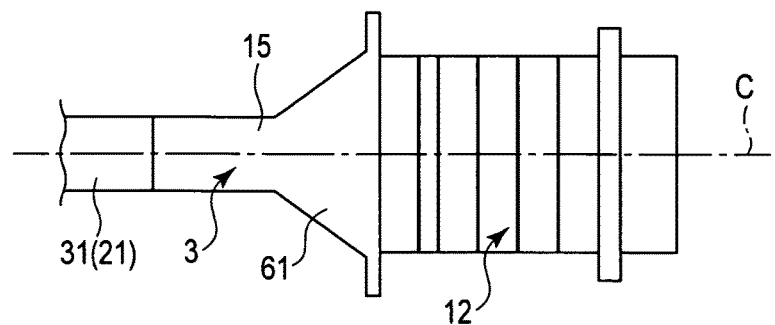
F I G. 19
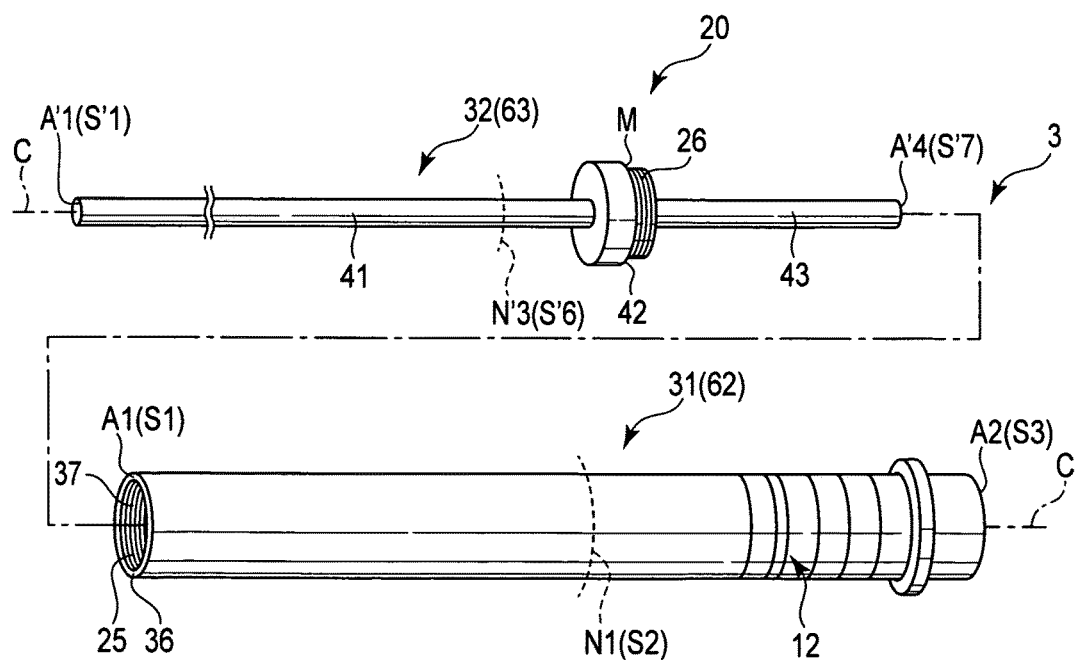
F I G. 20

ULTRASONIC TRANSMITTING UNIT

CROSS-REFERENCE TO RELATED APPLICATIONS

This is a Continuation Application of PCT Application No. PCT/JP2013/067893, filed Jun. 28, 2013 and based upon and claiming the benefit of priority from prior U.S. Provisional Application No. 61/697,074, filed Sep. 5, 2012, the entire contents of which are incorporated herein by reference.

BACKGROUND OF THE INVENTION

1. Field of the Invention

The present invention relates to an ultrasonic transmitting unit which extends along a longitudinal axis and which is configured to transmit an ultrasonic vibration from a proximal direction toward a distal direction.

2. Description of the Related Art

Ultrasonic transmitting units extending along a longitudinal axis are disclosed in the specification of Jpn. PCT National Publication No. 2010-535089 and the specification of Jpn. PCT National Publication No. 2000-506431. Each of the ultrasonic transmitting units includes a columnar portion, and an ultrasonic probe connected to a distal direction side of the columnar portion. A vibration generating portion such as an ultrasonic vibrator which is configured to generate an ultrasonic vibration is attached to the columnar portion. The ultrasonic vibration generated in the vibration generating portion is transmitted from a proximal direction toward a distal direction through the columnar portion and the ultrasonic probe. That is, in the ultrasonic transmitting unit, the ultrasonic vibration is transmitted from the proximal direction toward the distal direction.

Furthermore, in the columnar portion of each ultrasonic transmitting unit, a sectional area changing portion (a horn portion) in which a sectional area perpendicular to the longitudinal axis changes is provided. By this sectional area changing portion, an amplitude of the ultrasonic vibration generated in the vibration generating portion is enlarged.

BRIEF SUMMARY OF THE INVENTION

According to one aspect of the invention, an ultrasonic transmitting unit includes that: a first vibrating section which is configured to transmit an ultrasonic vibration and thereby configured to perform a vibration having an antinode position and a node position at a predetermined frequency; a second vibrating section which is configured to perform a vibration having an antinode position and a node position at the same predetermined frequency as in the first vibrating section, when the ultrasonic vibration is transmitted from the first vibrating section; a relay portion which relays between the first vibrating section and the second vibrating section, and which is configured to transmit the ultrasonic vibration from the first vibrating section to the second vibrating section, the relay portion being positioned at a position corresponding to one of the antinode position of the vibration in the first vibrating section and a position different from the antinode position and the node position of the vibration in the second vibrating section when the first vibrating section and the second vibrating section vibrate at the predetermined frequency; and a non-contact vibrating portion which is provided in the second vibrating section and extends from the relay portion toward a first vibrating section side in a state that the non-contact vibrating portion is not in contact with the first vibrating section.

According to one another aspect of the invention, an ultrasonic transmitting unit which is formed by connecting a first transmitting member and a second transmitting member, the first transmitting member being configured to perform a vibration having an antinode position and a node position at a predetermined frequency by an ultrasonic vibration, and the second transmitting member being configured to perform a vibration having an antinode position and a node position at the same predetermined frequency as in the first transmitting member by the ultrasonic vibration, wherein the first transmitting member includes: a first relay portion which is positioned at a position corresponding to one of the antinode position of the vibration in the first transmitting member when the first transmitting member vibrates at the predetermined frequency, and which abuts on the second transmitting member connected to the first transmitting member, and the second transmitting member includes: a second rely portion which is positioned at a position different from the antinode position and the node position of the vibration in the second transmitting member when the second transmitting member vibrates at the predetermined frequency, and which abuts on the first relay portion of the first transmitting member connected to the second transmitting member, the second relay portion being configured to transmit the ultrasonic vibration toward a first transmitting direction from the first relay portion of the first transmitting member to the second transmitting member; and a non-contact vibrating portion which extends from the second relay portion toward a first transmitting member side in a state that the non-contact vibrating portion is not in contact with the first transmitting member, in the second transmitting member in a state that the second relay portion abuts on the first relay portion of the first transmitting member, when an opposite direction with respect to the first transmitting direction is a second transmitting direction.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a sectional view schematically showing an internal configuration of a vibrator case according to the first embodiment;

FIG. 3 is a perspective view schematically showing a configuration of an ultrasonic transmitting unit according to the first embodiment;

FIG. 16 is a sectional view schematically showing a configuration of an ultrasonic probe according to a second modification;

FIG. 17 is a sectional view schematically showing a configuration of an ultrasonic probe according to a third modification;

FIG. 18 is a sectional view schematically showing a configuration of an ultrasonic probe according to a fourth modification;

FIG. 19 is a schematic view showing a configuration of an ultrasonic transmitting unit according to a fifth modification; and FIG. 20 is a perspective view schematically showing a configuration of an ultrasonic transmitting unit according to a sixth modification.

DETAILED DESCRIPTION OF THE INVENTION

First Embodiment

Figure 1:
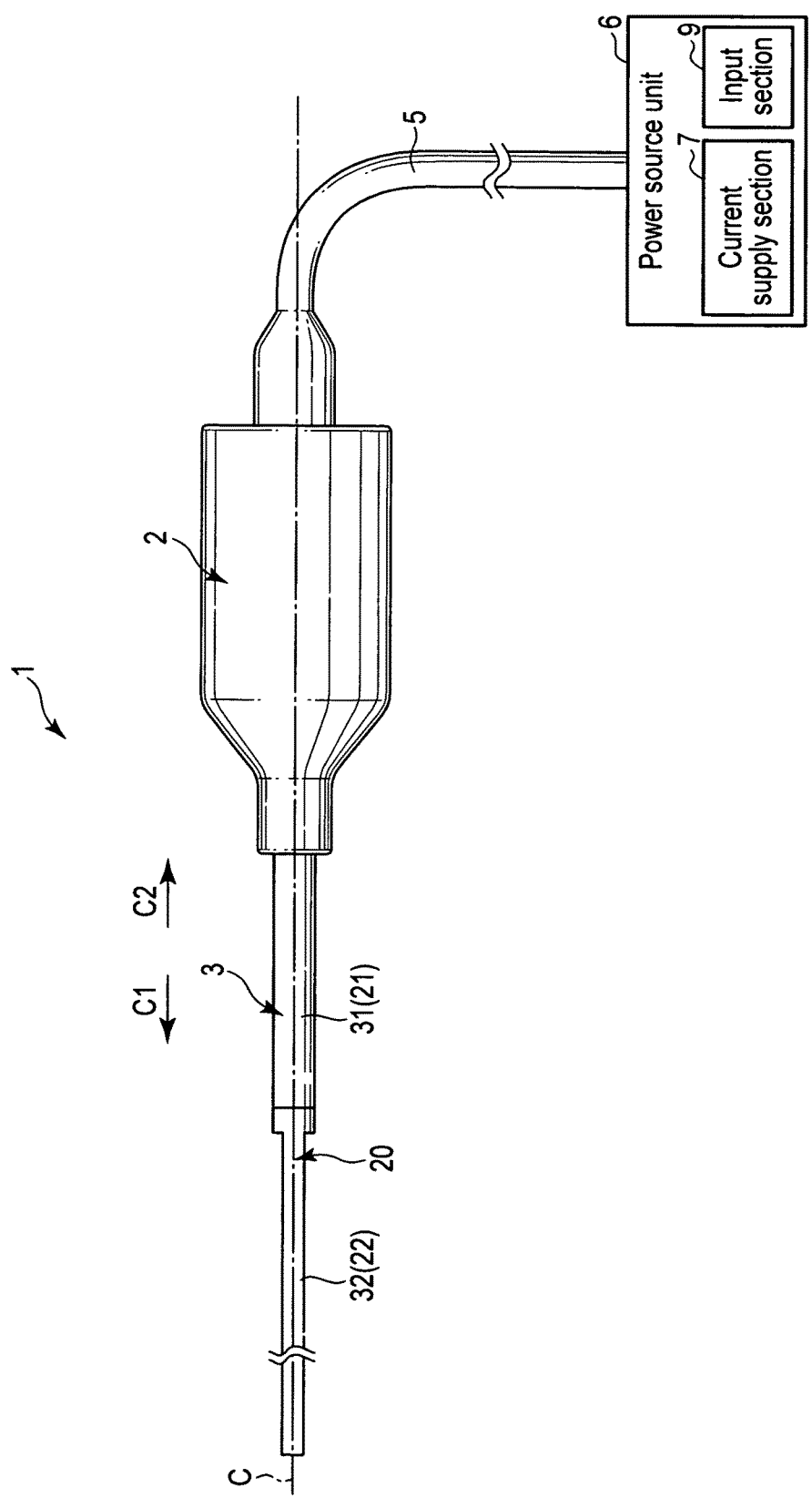
FIG. 1 is a schematic view showing an ultrasonic treatment device according to a first embodiment of the present invention.

A first embodiment of the present invention will be described with reference to FIG. 1 to FIG. 11. FIG. 1 is a view showing an ultrasonic treatment device 1 of the present embodiment. As shown in FIG. 1, the ultrasonic treatment device 1 has a longitudinal axis C. Here, one of two directions parallel to the longitudinal axis C is a distal direction (a direction of an arrow C1 of FIG. 1), and an opposite direction with respect to the distal direction is a proximal direction (a direction of an arrow C2 of FIG. 1). The ultrasonic treatment device 1 (an ultrasonic treatment system) includes a vibration generating unit 2, an ultrasonic transmitting unit 3 extending along the longitudinal axis C, and a power source unit 6 which generates energy to be supplied to the vibration generating unit 2. It is to be noted that in the present embodiment, the vibration generating unit 2 and the ultrasonic transmitting unit 3 constitute an ultrasonic treatment instrument.

The vibration generating unit 2 includes a vibrator case 11. A proximal end of the vibration generating unit 2 (the vibrator case 11) is connected to one end of a cable 5. The other end of the cable 5 is connected to the electric source unit 6. The power source unit 6 includes a current supply section 7 and an input section 9.

FIG. 2 is a view showing an internal configuration of the vibration generating unit 2. As shown in FIG. 2, in the oscillator case 11, there is disposed an ultrasonic vibrator 12 as an ultrasonic generating portion including piezoelectric elements 12A to 12C which is configured to convert a current into an ultrasonic vibration. The ultrasonic oscillator 12 is connected to one end of each of electric wiring lines 13A, 13B. The electric wiring lines 13A, 13B pass through an inside of the cable 5, and the other end of each electric wiring line 13A, 13B is connected to the current supply section 7 of the power source unit 6. The current supply section 7 supplies a current to the ultrasonic vibrator 12 via the electric wiring lines 13A, 13B, and the ultrasonic vibration is thereby generated in the ultrasonic vibrator 12.

FIG. 3 is a view showing a configuration of the ultrasonic transmitting unit 3. As shown in FIG. 2 and FIG. 3, the ultrasonic transmitting unit 3 includes a columnar portion 15. The ultrasonic vibrator 12 is attached to the columnar portion 15. The columnar portion 15 is inserted into a member constituting the ultrasonic vibrator 12 including the piezoelectric elements 12A to 12C, and the ultrasonic vibrator 12 is thereby attached to the columnar portion 15. The columnar portion 15 is attached to the vibrator case 11. An external thread portion 17 is formed in a distal portion of the columnar portion 15. Furthermore, the ultrasonic transmitting unit 3 includes a first probe member 21 as a first transmitting member and a second probe member 22 as a second transmitting member. The first probe member 21 and the second probe member 22 form an ultrasonic probe 20 as an ultrasonic transmitting body.

Figure 4:
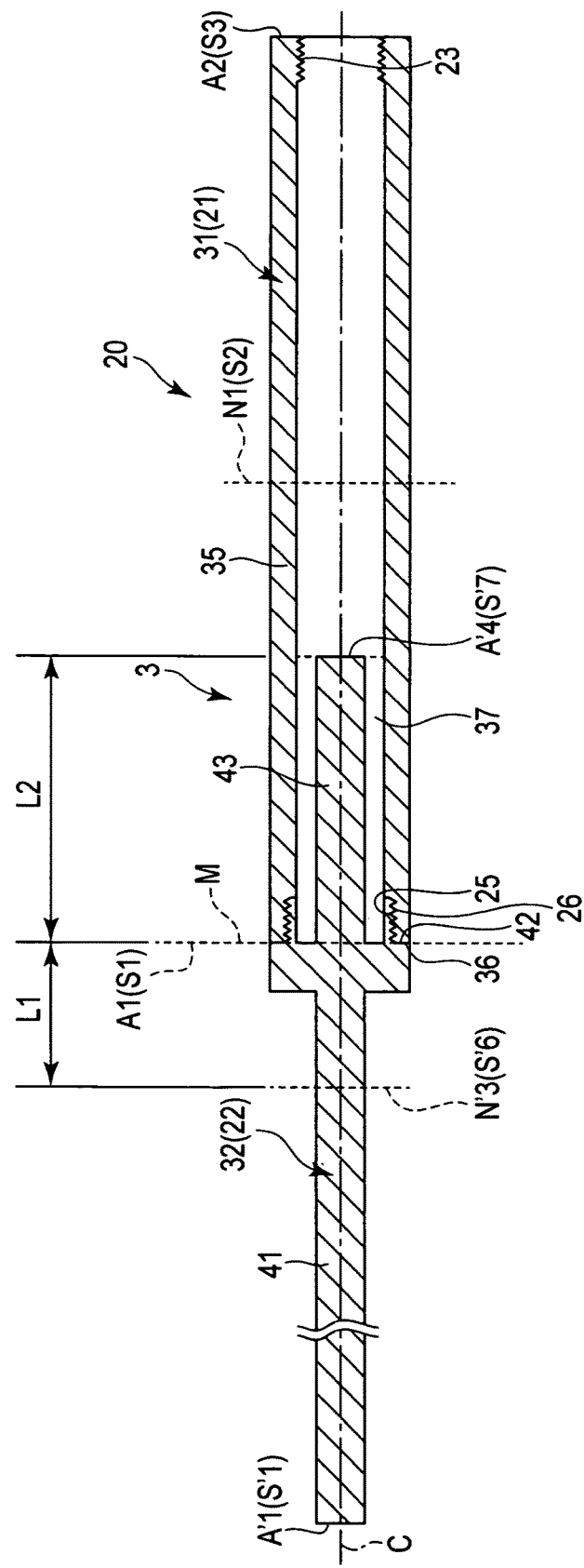
FIG. 4 is a sectional view schematically showing a configuration of an ultrasonic probe according to the first embodiment.

FIG. 4 is a view showing a configuration of the ultrasonic probe 20 in which the second probe member 22 is attached to the first probe member 21. As shown in FIG. 3 and FIG. 4, a proximal end of the first probe member 21 becomes a proximal end of the ultrasonic probe 20. An internal thread portion 23 is formed in a proximal portion of the first probe member 21. The external thread portion 17 of the columnar portion 15 is screwed to the internal thread portion 23, and the first probe member 21 is thereby attached to the columnar portion 15. Furthermore, an internal thread portion 25 is formed in a distal portion of the first probe member 21.

An external thread portion 26 is provided in the second probe member 22. The external thread portion 26 is screwed to the internal thread portion 25 of the first probe member 21, and the second probe member 22 is thereby attached to the first probe member 21. The first probe member 21 is attached to the columnar portion 15 and the second probe member 22 is attached to the first probe member 21, so that the ultrasonic transmitting unit 3 is formed.

In a state that the ultrasonic vibrator 12 is attached to the columnar portion 15, the ultrasonic vibration generated in the ultrasonic vibrator 12 is transmitted to the columnar portion 15 of the ultrasonic transmitting unit 3. Furthermore, in the ultrasonic transmitting unit 3, the ultrasonic vibration is transmitted from the proximal direction toward the distal direction. In consequence, the ultrasonic transmitting unit 3 performs a longitudinal vibration in which a vibrating direction and a transmitting direction are parallel to the longitudinal axis C.

The ultrasonic probe 20 includes a first vibrating section 31 which is configured to perform a first vibration at a predetermined frequency f0, when the ultrasonic vibration is transmitted, and a second vibrating section 32 which is configured to perform a second vibration at the same predetermined frequency f0 as in the first vibration, when the ultrasonic vibration is transmitted. In the present embodiment, the first probe member 21 becomes the first vibrating section 31 and the second probe member 22 becomes the second vibrating section 32.

In a state that the ultrasonic probe 20 is connected to the columnar portion 15, the ultrasonic vibration is transmitted from the columnar portion 15 to the first vibrating section 31. In consequence, the first vibrating section 31 performs the first vibration having first antinode positions A1, A2 and a first node position N1. Furthermore, the ultrasonic vibration is transmitted from the first vibrating section 31 to the second vibrating section 32. In consequence, the second vibrating section 32 performs the second vibration having second antinode positions A'1 to A'4 and second node positions N'1 to N'3.

It is to be noted that the first probe member 21 having a shape similar to that of the first vibrating section 31 vibrates at the predetermined frequency f0 even in a state that the second probe member 22 is not attached, when the ultrasonic vibration is transmitted. Furthermore, the second probe member 22 having a shape similar to that of the second vibrating section 32 vibrates at the predetermined frequency f0 even in the state that the second probe member is not attached to the first probe member 21, when the ultrasonic vibration is transmitted.

The first vibrating section 31 includes a first vibration main body portion 35. In the first vibration main body portion 35, a proximal side relay portion 36 is provided. The proximal side relay portion 36 is positioned at a distal end of the first vibration main body portion 35 (a distal end of the first vibrating section 31 in the present embodiment). Furthermore, in the first vibrating section 31, a hollow portion 37 is formed from the distal end of the first vibration main body portion 35 toward the proximal direction.

The second vibrating section 32 includes a second vibration main body portion 41. In the present embodiment, a distal end of the second vibration main body portion 41 becomes a distal end of the second vibrating section 32. In the second vibration main body portion 41, a distal side relay portion 42 is provided. The distal side relay portion 42 is positioned in a proximal side part of the second vibration main body portion 41. In a state that the second probe member 22 is attached to the first probe member 21, the distal side relay portion 42 abuts on the proximal side relay portion 36 of the first vibrating section 31. That is, a position of the proximal side relay portion 36 coincides with a position of the distal side relay portion 42 in the directions parallel to the longitudinal axis C. When the distal side relay portion 42 abuts on the proximal side relay portion 36, the ultrasonic vibration can be transmitted from the first vibrating section 31 to the second vibrating section 32.

Furthermore, the second vibrating section 32 includes a non-contact vibrating portion 43 extending from the distal side relay portion 42 toward the proximal direction side. A proximal end of the non-contact vibrating portion 43 becomes a proximal end of the second vibrating section 32. That is, the proximal end of the second vibrating section 32 is positioned in the non-contact vibrating portion 43. The second vibration main body portion 41 is continuous to a distal direction side of the non-contact vibrating portion 43. In a state that the distal side relay portion 42 abuts on the proximal side relay portion 36, the non-contact vibrating portion 43 is inserted in the hollow portion 37 of the first vibration main body portion 35. That is, the non-contact vibrating portion 43 extends from the proximal side relay portion 36 positioned at the distal end of the first vibrating section 31 toward the proximal direction side. The non-contact vibrating portion 43 does not come in contact with the first vibrating section 31 in a state that the non-contact vibrating portion is inserted into the hollow portion 37.

Next, a function and an effect of the ultrasonic transmitting unit 3 (the ultrasonic probe 20) will be described. When a treatment object such as a living tissue is treated by using the ultrasonic transmitting unit 3, a current of a predetermined value and a predetermined frequency is supplied from the current supply section 7 to the ultrasonic vibrator 12 via the electric wiring lines 13A, 13B by an operation in the input section 9. In consequence, the ultrasonic vibration is generated in the ultrasonic vibrator 12, and the ultrasonic vibration is transmitted to the ultrasonic probe 20 through the columnar portion 15. When the ultrasonic vibration is transmitted from the columnar portion 15 to the first vibrating section 31, the first vibrating section 31 performs the first vibration at the predetermined frequency f0. Furthermore, when the ultrasonic vibration is transmitted from the first vibrating section 31 to the second vibrating section 32, the second vibrating section 32 performs the second vibration at the same predetermined frequency f0 as in the first vibration. A distal portion of the ultrasonic probe 20 performs the treatment of the treatment object in a state that the ultrasonic probe 20 is vibrated. In this case, an amplitude of the ultrasonic vibration at the distal end of the ultrasonic probe 20 becomes larger, so that the treatment of the treatment object is efficiently performed by using the ultrasonic vibration.

Here, the first probe member 21 having the shape similar to that of the first vibrating section 31 vibrates at the predetermined frequency f0 even in the state that the second probe member 22 is not attached, when the ultrasonic vibration is transmitted. That is, the first vibrating section 31 (the first probe member 21) performs the first vibration at the predetermined frequency f0 even alone.

Figure 5:
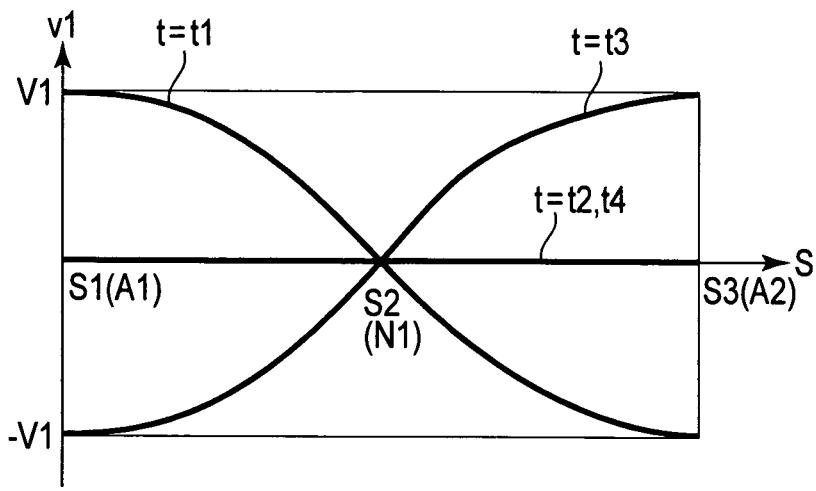
FIG. 5 is a schematic view showing a change of a first vibration with respect to a change of a position along a longitudinal axis in a first vibrating section, when the first vibrating section according to the first embodiment vibrates alone.

FIG. 5 is a view showing a change of a first vibration (v1) with respect to a change of a position S along the longitudinal axis C in the first vibrating section 31, when the first vibrating section 31 vibrates alone. It is to be noted that FIG. 5 shows the first vibration (v1) at time t=t1, t2, t3, and t4. As shown in FIG. 3 and FIG. 5, in the first vibration of the predetermined frequency f0, a position S1 which is the distal end of the first vibration main body portion 35 (the distal end of the first vibrating section 31) is the first antinode position A1. Furthermore, in the first vibration, a position S3 which is a proximal end of the first vibration main body portion 35 (a proximal end of the first vibrating section 31) becomes the first antinode position A2. In the first vibrating section 31, the distal end becomes the first antinode position A1 and the proximal end becomes the first antinode position A2, and hence the first vibrating section 31 can vibrate at the predetermined frequency f0. Furthermore, a position S2 positioned at an intermediate position between the position S1 and the position S3 becomes the first node position N1 of the first vibration.

Here, the amplitude of the first vibration at each position (S) along the longitudinal axis C in the first vibrating section 31 is a first amplitude. In the first vibration of the first vibrating section 31 alone, the first amplitude at the first antinode positions A1, A2 has a magnitude V1. Furthermore, in the first vibrating section 31, the proximal side relay portion 36 is positioned at the first antinode position A1. Here, the first antinode position A1 is one of the first antinode positions A1, A2, and becomes a relay antinode position where the proximal side relay portion 36 is positioned.

Furthermore, the second probe member 22 having a shape similar to that of the second vibrating section 32 vibrates at the predetermined frequency f0 even in a state that the second probe member is not attached to the first probe member 21, when the ultrasonic vibration is transmitted. That is, the second vibrating section 32 (the second probe member 22) performs a second vibration at the predetermined frequency f0 even alone.

Figure 6:
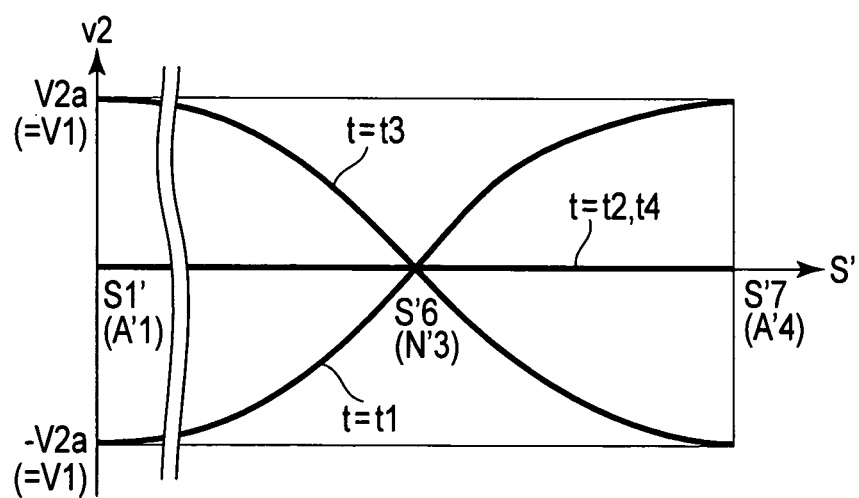
FIG. 6 is a schematic view showing a change of a second vibration with respect to a change of a position along a longitudinal axis in a second vibrating section, when the second vibrating section according to the first embodiment vibrates alone.

FIG. 6 is a view showing a change of the second vibration (v2) with respect to a change of a position S' along the longitudinal axis C in the second vibrating section 32, when the second vibrating section 32 vibrates alone. It is to be noted that FIG. 6 shows the second vibration (v2) at time t=t1, t2, t3, and t4. As shown in FIG. 3 and FIG. 6, in the second vibration, a position S'1 which is the distal end of the second vibration main body portion 41 (the distal end of the second vibrating section 32) becomes the second antinode position A'1. Furthermore, in the second vibration, a position S'7 which is a proximal end of the second vibrating section 32 (a proximal end of the non-contact vibrating portion 43) becomes the second antinode position A'4. In the second vibrating section 32, the distal end becomes the second antinode position A'1 and the proximal end becomes the second antinode position A'4, so that the second vibrating section 32 can vibrate at the predetermined frequency f0.

Furthermore, in the second vibrating section 32, positions S'2 to S'6 are positioned between the position S'1 and the position S'7 in the directions parallel to the longitudinal axis C. In the second vibration, the position S'3 becomes the second antinode position A'2 and the position S'5 becomes the second antinode position A'3. Furthermore, in the second vibration, the position S'2 becomes the second node position N'1, the position S'4 becomes the second node position N'2, and the position S'6 becomes the second node position N'3.

Here, an amplitude of the second vibration at each position (S') along the longitudinal axis C in the second vibrating section 32 is a second amplitude. In the second vibration of the second vibrating section 32 alone, the second amplitude at the second antinode positions A'1 to A'4 has a magnitude V2a. The magnitude V2a of the second amplitude at the second antinode positions A'1 to A'4 when the second vibrating section 32 vibrates alone is the same as the magnitude V1 of the first amplitude at the first antinode positions A1, A2 when the first vibrating section 31 vibrates alone. Here, the second antinode position A'1 positioned most distally among the second antinode positions A'1 to A'4 is the most distal antinode position.

Furthermore, the distal side relay portion 42 is positioned at a middle position M different from the second antinode positions A'1 to A'4 and the second node positions N'1 to N'3 of the second vibration. In the present embodiment, the middle position M is positioned between the second node position N'3 and the second antinode position A'4. That is, the middle position M is positioned between the third distally second-node position N'3 and the fourth distally second-antinode position A'4.

Furthermore, the ultrasonic probe 20 in which the second probe member 22 is attached to the first probe member 21 also vibrates at the predetermined frequency f0, when the ultrasonic vibration is transmitted. In this case, the first vibrating section 31 performs the first vibration at the predetermined frequency f0 and the second vibrating section 32 performs the second vibration at the predetermined frequency f0.

Figure 7:
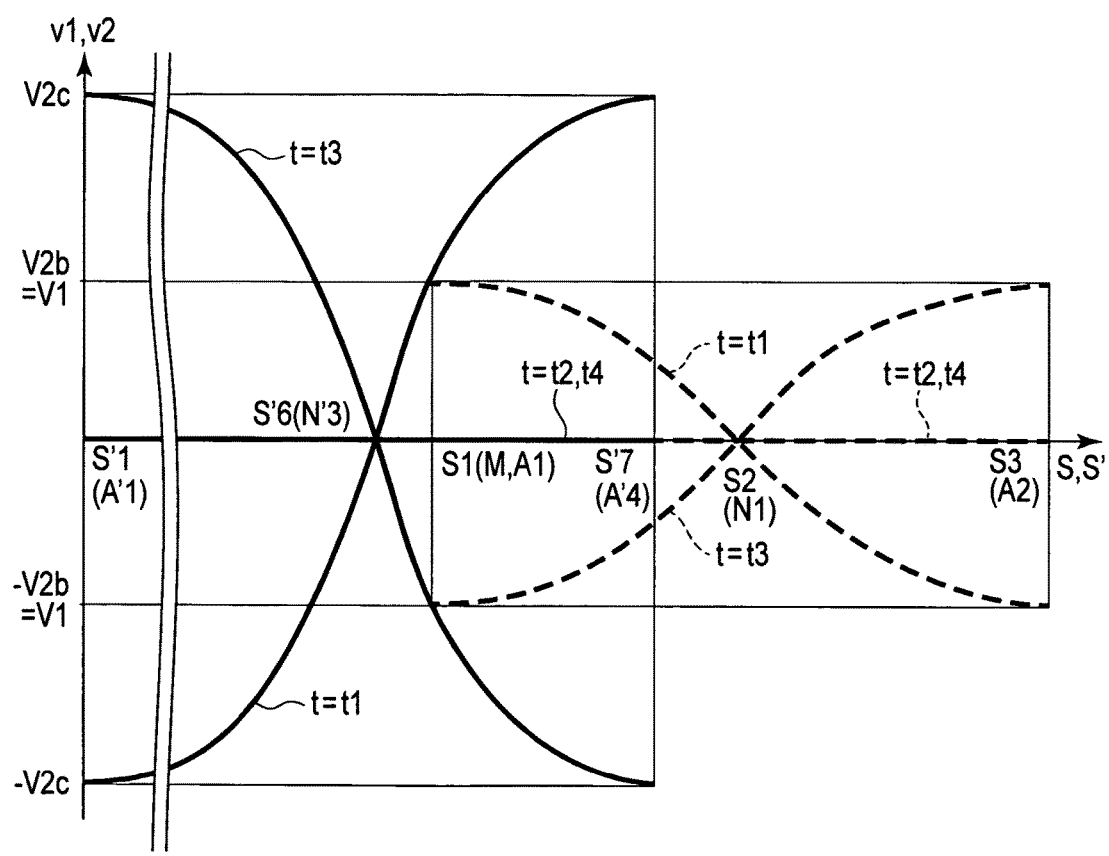
FIG. 7 is a schematic view showing the change of the first vibration and the change of the second vibration with respect to a change of a position along the longitudinal axis in the ultrasonic probe, when the ultrasonic probe according to the first embodiment vibrates.

FIG. 7 is a view showing the change of the first vibration (v1) and the change of the second vibration (v2) with respect to a change of a position (S, S') along the longitudinal axis C in the ultrasonic probe 20, when the ultrasonic probe 20 in which the second probe member 22 is attached to the first probe member 21 vibrates. It is to be noted that FIG. 7 shows the first vibration (v1) and the second vibration (v2) at time t=t1, t2, t3, and t4. Furthermore, FIG. 7 shows the first vibration of the first vibrating section 31 by a dotted line, and shows the second vibration of the second vibrating section 32 by a solid line.

As shown in FIG. 4 and FIG. 7, also in a case where the ultrasonic probe 20 vibrates, the first vibrating section 31 performs the first vibration at the predetermined frequency f0 in the same manner as in a case where the first vibrating section 31 performs the first vibration alone. Therefore, the first antinode positions A1, A2 and the first node position N1 in the directions parallel to the longitudinal axis C are the same positions as the first antinode positions A1, A2 and the first node position N1 when the first vibrating section 31 alone performs the first vibration. Furthermore, also when the ultrasonic probe 20 vibrates at the predetermined frequency f0, the first amplitude at the first antinode positions A1, A2 has the magnitude V1 in the same manner as in the case where the first vibrating section 31 vibrates alone.

Furthermore, also when the ultrasonic probe 20 vibrates, the second vibrating section 32 performs the second vibration at the predetermined frequency f0 in the same manner as in a case where the second vibrating section 32 alone performs the second vibration. Therefore, the second antinode positions A'1 to A'4 and the second node positions N'1 to N'3 in the directions parallel to the longitudinal axis C are the same positions as the second antinode positions A'1 to A'4 and the second node positions N'1 to N'3 in the case where the second vibrating section 32 performs the second vibration alone.

Here, in the ultrasonic probe 20, the ultrasonic vibration is transmitted from the first vibrating section 31 to the second vibrating section 32 via the proximal side relay portion 36 and the distal side relay portion 42. The proximal side relay portion 36 is positioned at the first antinode position A1 of the first vibration and the distal side relay portion 42 is positioned at the middle position M of the second vibration. In the ultrasonic probe 20, the distal side relay portion 42 abuts on the proximal side relay portion 36 and the first antinode position A1 coincides with the middle position M in the directions parallel to the longitudinal axis C.

Figure 8:
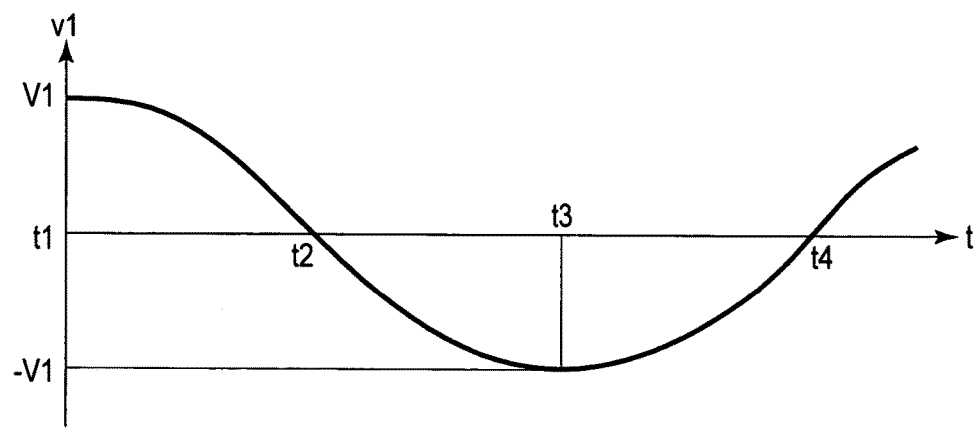
FIG. 8 is a schematic view showing a change of the first vibration with time at a relay antinode position of the first vibrating section, when the ultrasonic probe according to the first embodiment vibrates.
Figure 9:
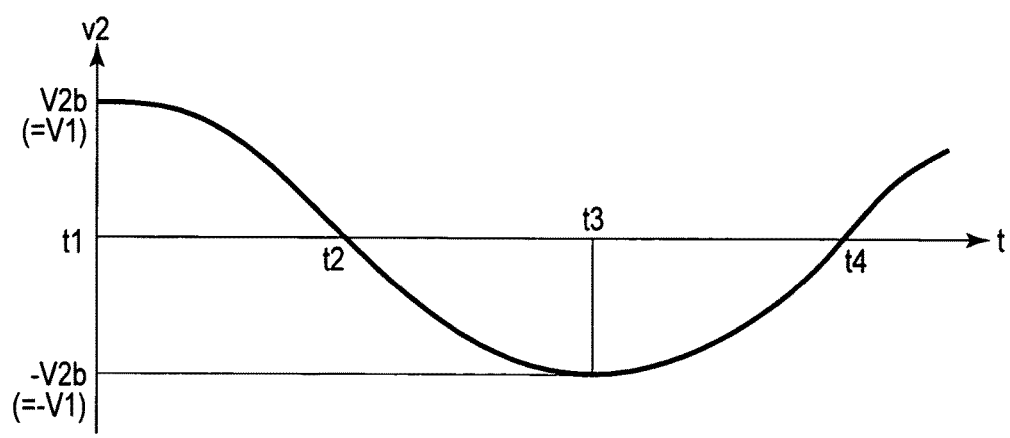
FIG. 9 is a schematic view showing a change of the second vibration with time at a middle position of the second vibrating section, when the ultrasonic probe according to the first embodiment vibrates.

FIG. 8 is a view showing a change of the first vibration with time at the relay antinode position (A1), when the ultrasonic probe 20 in which the second vibrating section 32 is attached to the first vibrating section 31 vibrates at the predetermined frequency f0. Furthermore, FIG. 9 is a view showing a change of the second vibration with time at the middle position M, when the ultrasonic probe 20 vibrates at the predetermined frequency f0. As shown in FIG. 7 to FIG. 9, when the ultrasonic probe 20 vibrates, the first amplitude of the first vibration at the relay antinode position (A1) has the magnitude V1. Furthermore, the second amplitude of the second vibration at the middle position M has a magnitude V2b.

Here, the distal side relay portion 42 abuts on the proximal side relay portion 36, and the first antinode position A1 matches the middle position M in the directions parallel to the longitudinal axis C. Therefore, the magnitude V2b of the second amplitude at the middle position M is the same as the magnitude V1 of the first amplitude at the relay antinode position A1. Furthermore, the first vibration at the relay antinode position (the first antinode position) A1 and the second vibration at the middle position M have the same phase with respect to each other.

When the ultrasonic probe 20 vibrates, the magnitude V2b of the second amplitude at the middle position M different from the second antinode positions A'1 to A'4 becomes the same as the magnitude V1 of the first amplitude at the first antinode positions A1, A2 of the first vibration. In the second vibration, the second amplitude at the second antinode positions A'1 to A'4 is larger than the second amplitude at the middle position M. Therefore, when the ultrasonic probe 20 (the ultrasonic transmitting unit 3) vibrates at the predetermined frequency f0, a magnitude V2c of the second amplitude at the second antinode positions A'1 to A'4 is larger than the magnitude V1 of the first amplitude at the first antinode positions A1, A2 of the first vibration.

As described above, there is not disposed a sectional area changing portion (a horn portion) in which a sectional area perpendicular to the longitudinal axis C changes, but it is possible to enlarge the second amplitude of the ultrasonic vibration at the most distal antinode position (A'1) positioned at the distal end of the second vibrating section 32 (the distal end of the ultrasonic probe 20). In consequence, even when the sectional area changing portion is not provided, the treatment of the treatment object is efficiently performed by using the ultrasonic vibration.

Figure 10:
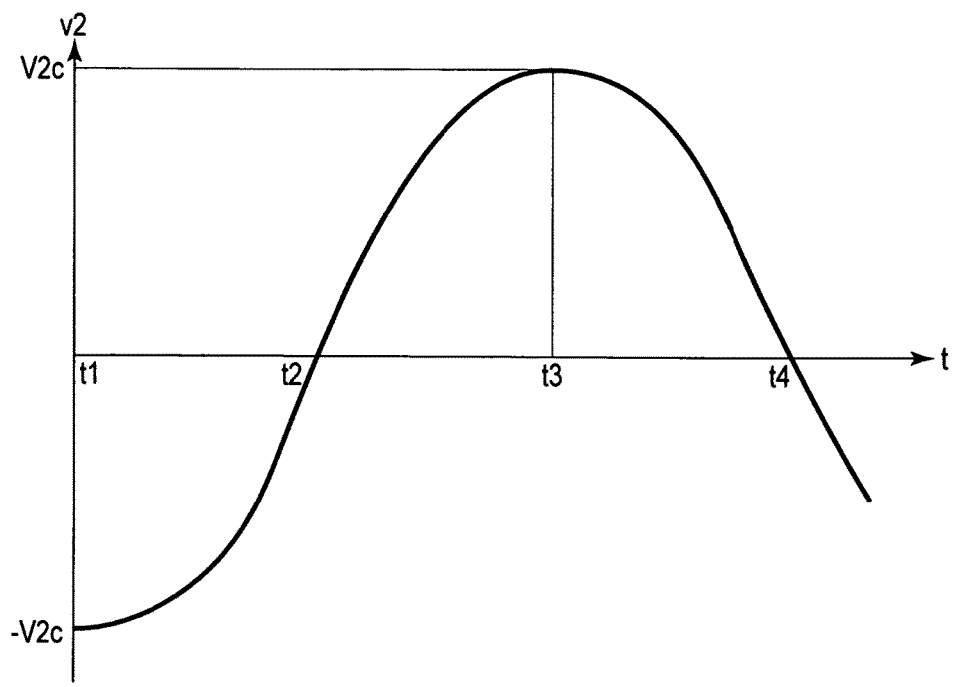
FIG. 10 is a schematic view showing the change of the second vibration with time at a most distal antinode position of the second vibrating section, when the ultrasonic probe according to the first embodiment vibrates.

FIG. 10 is a view showing the change of the second vibration with time at the most distal antinode position (A'1), when the ultrasonic probe 20 vibrates at the predetermined frequency f0. As described above, the second antinode position A'1, which is the most distal antinode position, is positioned at the distal end of the second vibrating section 32. Furthermore, as shown in FIG. 10, the magnitude V2c of the second amplitude at the second antinode position A'1 is larger than the magnitude V1 of the first amplitude at the first antinode position (A1), which is the relay antinode position. Furthermore, in the second vibration, the middle position M is positioned between the second node position N'3 and the second antinode position A'4. In this case, the second vibration at the second antinode position (the most distal antinode position) A'1 has an opposite phase with respect to the first vibration at the first antinode position (the relay antinode position) A1.

Here, n is a natural number. When the middle position M is positioned between the n-th distally second node position N'n and the (n+1)-th distally second antinode position A'n+1, a relation between the second vibration at the second antinode position (the most distal antinode position) A'1 and the first vibration at the first antinode position (the relay antinode position) is similar to that of the present embodiment. That is, the second vibration at the second antinode position (the most distal antinode position) A'1 has an opposite phase with respect to the first vibration at the first antinode position (the relay antinode position) A1.

Figure 11:
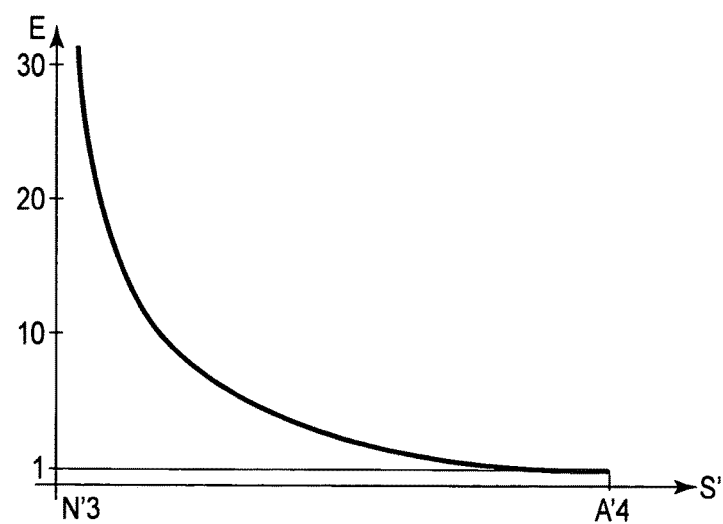
FIG. 11 is a schematic view showing an enlargement ratio of a second amplitude at a second antinode position of the second vibration with respect to a first amplitude at a first antinode position of the first vibration, when a position of the middle position is changed along the longitudinal axis between a nearby node position and a nearby antinode position in the second vibrating section according to the first embodiment.

In the present embodiment, the second node position N'3 becomes a nearby node positioned closest to the middle position M among the second node positions N'1 to N'3. Furthermore, the second antinode position A'4 is a nearby antinode position positioned closest to the middle position M among the second antinode positions A'1 to A'4. FIG. 11 shows an enlargement ratio E of the second amplitude at the second antinode positions A'1 to A'4 of the second vibration with respect to the first amplitude at the first antinode positions A1, A2 of the first vibration, when a position of the middle position M is changed along the longitudinal axis C between the nearby node position (N'3) and the nearby antinode position (A'4) in the second vibrating section 32.

As described above, the magnitude V2b of the second amplitude at the middle position M is the same as the magnitude V1 of the first amplitude at the first antinode position A1 which is the relay antinode position. Therefore, regardless of the positional change of the middle position along the longitudinal axis C, the magnitude V2b of the second amplitude at the middle position M is the same as the magnitude V1 of the first amplitude at the first antinode positions A1, A2. That is, the magnitude V2b of the second amplitude at the middle position M does not change in accordance with the positional change of the middle position M along the longitudinal axis C.

On the other hand, as the position of the middle position M comes closer to the nearby node position (N'3), a ratio E' of the magnitude V2c of the second amplitude at each of the second antinode positions A'1 to A'4 with respect to the magnitude V2b of the second amplitude at the middle position M becomes larger. The magnitude V1 of the first amplitude at the relay antinode position (A1) is the same as the magnitude V2b of the second amplitude at the middle position M. Therefore, as shown in FIG. 11, as the position of the middle position M comes closer to the nearby node position (N'3), the enlargement ratio E of the magnitude V2c of the second amplitude at each of the second antinode positions A'1 to A'4 with respect to the magnitude V1 of the first amplitude at the first antinode positions A1, A2 becomes larger.

Here, a dimension along the longitudinal axis C between the nearby node position (N'3) and the middle position M is a first axis parallel dimension L1, and a dimension along the longitudinal axis C between the nearby antinode position (A'4) and the middle position M is a second axis parallel dimension L2. When the first axis parallel dimension L1 is smaller than the second axis parallel dimension L2, the enlargement ratio E of the second amplitude at the second antinode positions A'1 to A'4 with respect to the first amplitude at the first antinode positions A1, A2 becomes larger. In the present embodiment, the first axis parallel dimension L1 and the second axis parallel dimension L2 are preferably set so that the enlargement ratio E is 3 or more.

In consequence, the second amplitude of the second vibration at the most distal antinode position (A'1) positioned at the distal end of the second vibrating section 32 is further enlarged. Therefore, the treatment of the treatment object is further efficiently performed by using the ultrasonic vibration.

It is to be noted that when the middle position M coincides with the second antinode position A'4 which is the nearby antinode position, a value of the enlargement ratio E of the second amplitude at the second antinode positions A'1 to A'4 with respect to the first amplitude at the first antinode positions A1, A2 is 1, and the second amplitude at the second antinode positions A'1 to A'4 is not enlarged. On the other hand, when the middle position M coincides with the second node position N'3 which is the nearby node position, the enlargement ratio E of the second amplitude at the second antinode positions A'1 to A'4 with respect to the first amplitude at the first antinode position infinitely becomes larger, and the second amplitude at the second antinode positions A'1 to A'4 infinitely becomes larger. When a portion where the second amplitude infinitely becomes larger is generated in the ultrasonic probe 20, transmission properties of the ultrasonic vibration in the ultrasonic probe 20 deteriorate. From the abovementioned viewpoint, the middle position M of the second vibration is different from the second antinode positions A'1 to A'4 and the second node positions N'1 to N'3, so that the second amplitude of the ultrasonic vibration at the distal end of the second vibrating section 32 (the distal end of the ultrasonic probe 20) is effectively enlarged.

As described above, in the ultrasonic probe 20, the sectional area changing portion in which the sectional area perpendicular to the longitudinal axis C changes is not provided, but the second amplitude of the ultrasonic vibration at the distal end of the second vibrating section 32 (the distal end of the ultrasonic probe 20) can be enlarged. In consequence, even when the sectional area changing portion is not provided, the treatment of the treatment object can efficiently be performed by using the ultrasonic vibration. Furthermore, the sectional area changing portion is not disposed, which can reduce labor and cost in the manufacturing of the elongated ultrasonic transmitting unit 3.

(Modifications)

Figure 12:
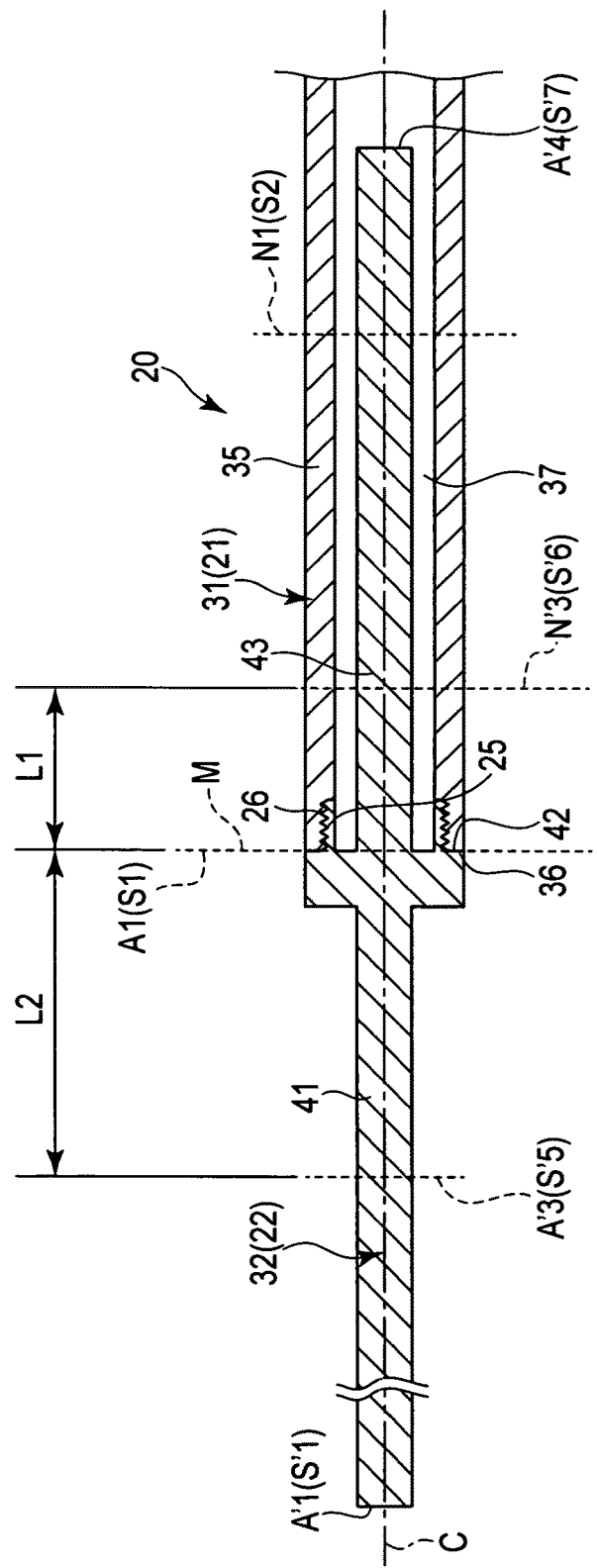
FIG. 12 is a sectional view schematically showing a configuration of an ultrasonic probe according to a first modification.
Figure 13:
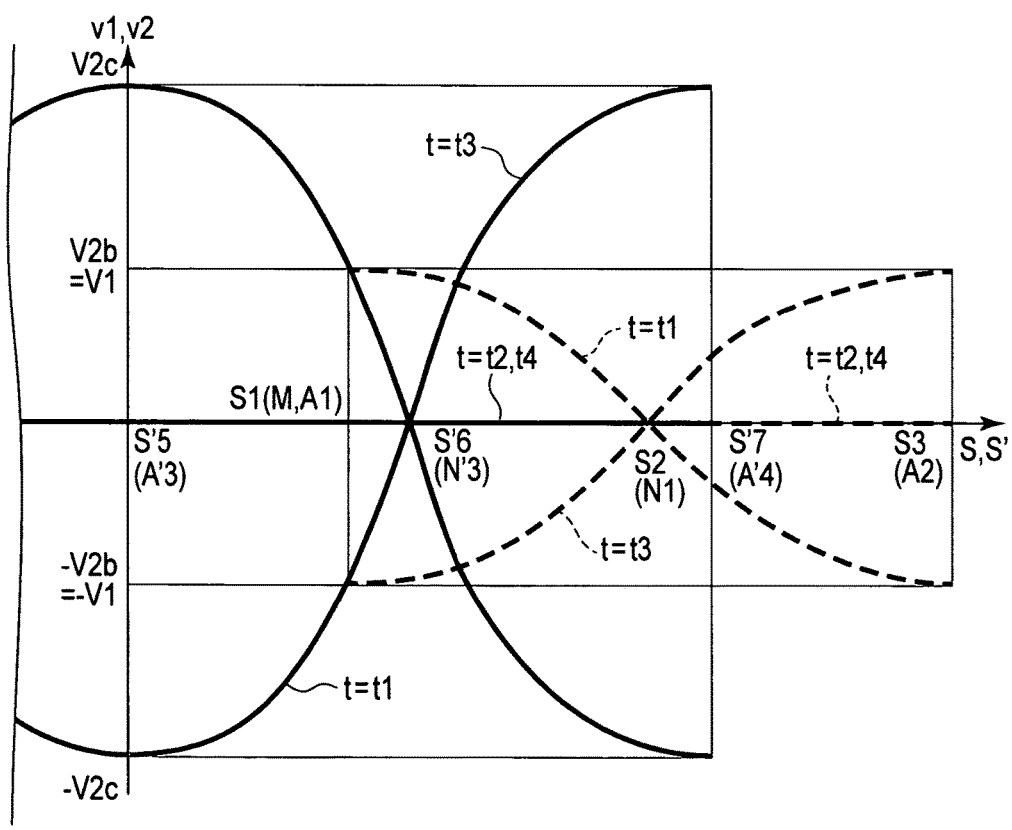
FIG. 13 is a schematic view showing a change of a first vibration and a change of a second vibration with respect to a change of a position along a longitudinal axis in the ultrasonic probe, when the ultrasonic probe according to the first modification vibrates.

It is to be noted that in the first embodiment, the middle position M where the distal side relay portion 42 is disposed is positioned between the second node position N'3 and the second antinode position A'4, but it is not limited to this example. FIG. 12 is a view showing a configuration of an ultrasonic probe 20 in which a second probe member 22 is attached to a first probe member 21 in a first modification. FIG. 13 is a view showing a change of a first vibration (v1) and a change of a second vibration (v2) with respect to a change of a position (S, S') along a longitudinal axis C in the ultrasonic probe 20, when the ultrasonic probe 20 in which a second vibrating section 32 is attached to a first vibrating section 31 vibrates at a predetermined frequency f0. It is to be noted that FIG. 13 shows the first vibration (v1) and the second vibration (v2) at time t=t1, t2, t3, and t4. Furthermore, FIG. 13 shows the first vibration of the first vibrating section 31 by a dotted line, and shows the second vibration of the second vibrating section 32 by a solid line.

As shown in FIG. 12 and FIG. 13, also in the present embodiment, first antinode positions A1, A2, a first node position N1, second antinode positions A'1 to A'4 and second node positions N'1 to N'3 are positioned at the same positions as in the first embodiment. Furthermore, the first antinode position A1 is a relay antinode position where a proximal side relay portion 36 is positioned. Furthermore, a middle position M where a distal side relay portion 42 is positioned is different from the second antinode positions A'1 to A'4 and the second node positions N'1 to N'3 of the second vibration.

However, in the present modification, differing from the first embodiment, the middle position M is positioned between the second antinode position A'3 and the second node position N'3. That is, the middle position M is positioned between the third distally second-antinode position A'3 and the third distally second-node position N'3.

Similarly to the first embodiment, also in the present modification, a magnitude V2b of a second amplitude at the middle position M is the same as a magnitude V1 of a first amplitude at the first antinode position A1 (A2). Furthermore, the first vibration at the relay antinode position (the first antinode position) A1 and the second vibration at the middle position M have the same phase with respect to each other. In the second vibration, the magnitude V2b of the second amplitude at the middle position M different from the second antinode positions A'1 to A'4 is the same as the magnitude V1 of the first amplitude at the first antinode positions A1, A2 of the first vibration. Therefore, a magnitude V2c of the second amplitude at the second antinode positions A'1 to A'4 of the second vibration is larger than the magnitude V1 of the first amplitude at the first antinode positions A1, A2 of the first vibration.

Figure 14:
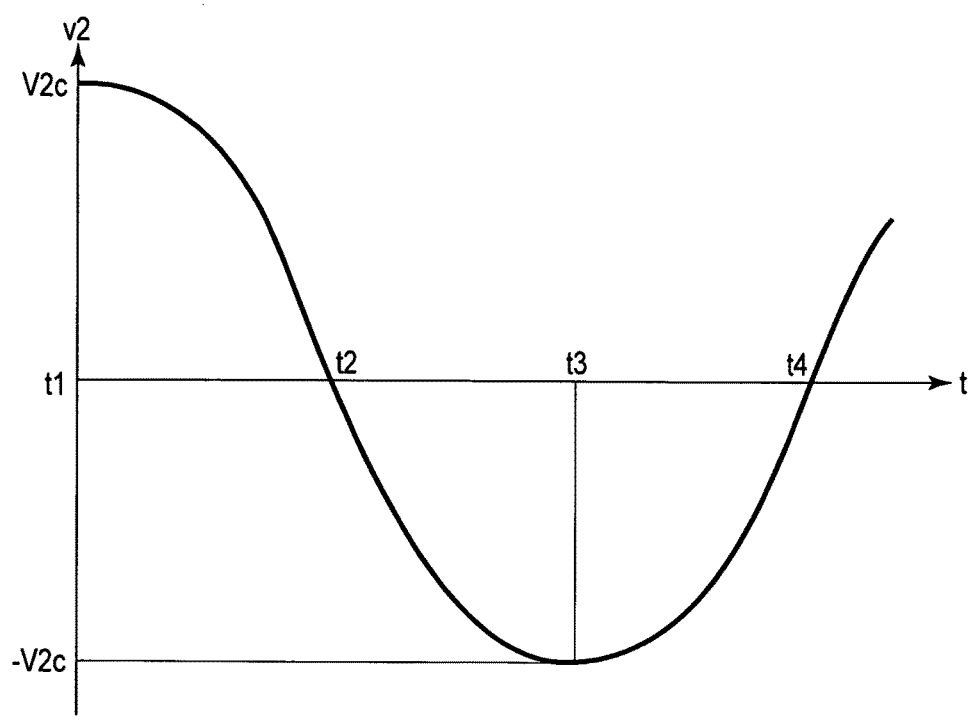
FIG. 14 is a schematic view showing a change of the second vibration with time at a most distal antinode position of a second vibrating section, when the ultrasonic probe according to the first modification vibrates.

FIG. 14 is a view showing a change of the second vibration with time at the most distal antinode position (A'1), when the ultrasonic probe 20 vibrates. As described above, the second antinode position A'1 which is the most distal antinode position is positioned at a distal end of the second vibrating section 32. Furthermore, as shown in FIG. 14, the magnitude V2c of the second amplitude at the second antinode position A'1 is larger than the magnitude V1 of the first amplitude at the first antinode position (A1) which is the relay antinode position. Furthermore, in the second vibration, the middle position M is positioned between the second antinode position A'3 and the second node position N'3. In this case, the second vibration at the second antinode position (the most distal antinode position) A'1 has the same phase as in the first vibration at the first antinode position (the relay antinode position) A1.

Here, n is a natural number. When the middle position M is positioned between the n-th distally second antinode position A'n and the n-th distally second node position N'n, a relation between the second vibration at the second antinode position (the most distal antinode position) A'1 and the first vibration at the first antinode position (the relay antinode position) A1 is similar to that of the present modification. That is, the second vibration at the second antinode position (the most distal antinode position) A'1 has the same phase as the first vibration at the first antinode position (the relay antinode position) A1.

In the first embodiment, when the middle position M is positioned between the n-th distally second node position N'n and the (n+1)-th distally second antinode position A'n+1, the second vibration at the second antinode position (the most distal antinode position) A'1 has an opposite phase with respect to the first vibration at the first antinode position (the relay antinode position) A1. On the other hand, in the present modification, when the middle position M is positioned between the n-th distally second antinode position A'n and the n-th distally second node position N'n, the second vibration at the second antinode position (the most distal antinode position) A'1 has the same phase as the first vibration at the first antinode position (the relay antinode position) A1. That is, when a position of the middle position M in the second vibrating section 32 is changed in directions parallel to the longitudinal axis C, a phase relation of the second vibration at the second antinode position (the most distal antinode position) A'1 with respect to the first vibration at the first antinode position (the relay antinode position) A1 is changed. That is, when the position of the middle position M is changed in the directions parallel to the longitudinal axis C, the distal side relay portion 42 positioned at the middle position M becomes a phase changing portion by which the phase relation of the second vibration at the second antinode position (the most distal antinode position) A'1 with respect to the first vibration at the first antinode position (the relay antinode position) A1 is changed.

Figure 15:
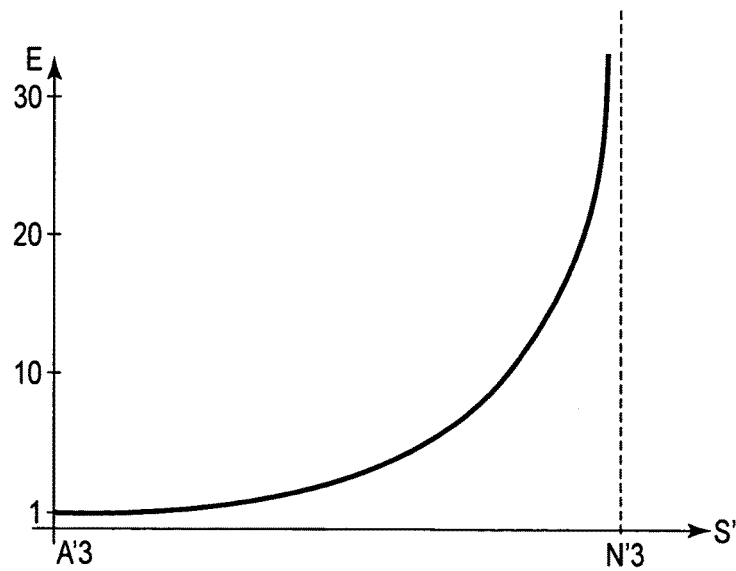
FIG. 15 is a schematic view showing an enlargement ratio of a second amplitude at a second antinode position of the second vibration with respect to a first amplitude at a first antinode position of the first vibration, when a position of the middle position is changed along the longitudinal axis between a nearby node position and a nearby antinode position in the second vibrating section according to the first modification.

In the present modification, the second node position N'3 is a nearby node position positioned closest to the middle position M among the second node positions N'1 to N'3. Furthermore, the second antinode position A'3 is a nearby antinode position positioned closest to the middle position M among the second antinode positions A'1 to A'4. FIG. 15 shows an enlargement ratio E of the second amplitude at each of the second antinode positions A'1 to A'4 of the second vibration with respect to the first amplitude at each of the first antinode positions A1, A2 of the first vibration, when the position of the middle position M in the second vibrating section 32 is changed along the longitudinal axis C between the nearby node position (N'3) and the nearby antinode position (A'3).

As described above, the magnitude V2b of the second amplitude at the middle position M is the same as the magnitude V1 of the first amplitude at the first antinode position A1 which is the relay antinode position. Therefore, the magnitude V2b of the second amplitude at the middle position M is the same as the magnitude V1 of the first amplitude at the first antinode positions A1, A2, regardless of the positional change of the middle position M along the longitudinal axis C. That is, by the positional change of the middle position M along the longitudinal axis C, the magnitude V2b of the second amplitude of the second vibration at the middle position M does not change.

On the other hand, as the position of the middle position M comes closer to the nearby node position (N'3), a ratio E' of the magnitude V2c of the second amplitude at each of the second antinode positions A'1 to A'4 with respect to the magnitude V2b of the second amplitude at the middle position M becomes larger. The magnitude V1 of the first amplitude at the relay antinode position (A1) is the same as the magnitude V2b of the second amplitude at the middle position M. Therefore, as shown in FIG. 15, as the position of the middle position M comes closer to the nearby node position (N'3), the enlargement ratio E of the magnitude V2c of the second amplitude at the second antinode positions A'1 to A'4 with respect to the magnitude V1 of the first amplitude at the first antinode positions A1, A2 becomes larger.

Here, a dimension along the longitudinal axis C between the nearby node position (N'3) and the middle position M is a first axis parallel dimension L1, and a dimension along the longitudinal axis C between the nearby antinode position (A'3) and the middle position M is a second axis parallel dimension L2. The first axis parallel dimension L1 is smaller than the second axis parallel dimension L2, and hence the enlargement ratio E of the second amplitude at the second antinode positions A'1 to A'4 with respect to the first amplitude at the first antinode positions A1, A2 becomes larger. In consequence, the second amplitude of the second vibration at the most distal antinode position (A'1) positioned at the distal end of the second vibrating section 32 is further enlarged. Therefore, the treatment of the treatment object is further efficiently performed by using the ultrasonic vibration.

Furthermore, in the first embodiment, from the first probe member 21 having the shape similar to that of the first vibrating section 31 and the second probe member 22 having the shape similar to that of the second vibrating section 32, the first vibrating section 31 and the second vibrating section 32 are formed, but it is not limited to this example. For example, as a second modification shown in FIG. 16, a first vibrating section 31 and a second vibrating section 32 may be formed from a third probe member 51 and a fourth probe member 52. In the present modification, an engagement groove 53 is provided in the third probe member 51, and an engaging projection 55 is provided in the fourth probe member 52. Furthermore, when the engaging projection 55 engages with the engagement groove 53, the fourth probe member 52 is attached to the third probe member 51 to form the ultrasonic probe 20.

In the present modification, the engaging projection 55 is positioned to a proximal direction side with respect a proximal side relay portion 36 and a distal side relay portion 42. Therefore, at a position located to the proximal direction side from the proximal side relay portion 36 and the distal side relay portion 42, the fourth probe member 52 is attached to the third probe member 51. Therefore, in the present modification, the third probe member 51 becomes a part of the first vibrating section 31. Furthermore, the fourth probe member 52 becomes a part of the first vibrating section 31 other than the third probe member and becomes the second vibrating section 32. Furthermore, in the present modification, at the position located to the proximal direction side with respect to the proximal side relay portion 36 and the distal side relay portion 42, the fourth probe member 52 is attached to the third probe member 51, and hence the distal side relay portion 42 is continuous with the proximal side relay portion 36.

Furthermore, in the present modification, a distal end of the third probe member 51 is positioned to the proximal direction side from the proximal side relay portion 36, and hence the distal end of the third probe member 51 is a position different from a first antinode position (a relay antinode position) A1 of a first vibration. Therefore, in a state that the fourth probe member 52 is not attached, the third probe member 51 does not vibrate at a predetermined frequency f0 even when ultrasonic vibration is transmitted. In the state that the fourth probe member 52 is not attached, the third probe member 51 does not vibrate, and hence an erroneous actuation is effectively prevented in a treatment in which the ultrasonic vibration is used. A distal end of the fourth probe member 52 is positioned at a second antinode position A'1 of a second vibration, and a proximal end thereof is positioned at a second antinode position A'4 of the second vibration. The fourth probe member 52, to which the ultrasonic vibration is transmitted, vibrates at the predetermined frequency f0 even in a state that the fourth probe member is not attached to the third probe member 51.

Also in the present modification, the fourth probe member 52 is attached to the third probe member 51, so that the first vibrating section 31 and the second vibrating section 32 similar to those of the first embodiment are formed. Therefore, when the ultrasonic probe 20 vibrates at the predetermined frequency f0, a magnitude V2c of a second amplitude at the second antinode positions A'1 to A'4 of a second vibration is larger than a magnitude V1 of the first amplitude at the first antinode positions A1, A2 of the first vibration.

Furthermore, as a third modification shown in FIG. 17, a first vibrating section 31 and a second vibrating section 32 may integrally be formed from a fifth probe member 57. In the present modification, the first vibrating section 31 and the second vibrating section 32 are integrally formed from the fifth probe member 57, and hence a distal side relay portion 42 is continuous with a proximal side relay portion 36. Also in the present modification, the first vibrating section 31 and the second vibrating section 32 similar to those of the first embodiment are formed. Therefore, when an ultrasonic probe 20 vibrates at a predetermined frequency f0, a magnitude V2c of a second amplitude at second antinode positions A'1 to A'4 of a second vibration is larger than a magnitude V1 of a first amplitude at first antinode positions A1, A2 of a first vibration.

Furthermore, in the first embodiment, the hollow portion 37 is formed in the first vibrating section 31, and the non-contact vibrating portion 43 of the second vibrating section 32 is inserted into the hollow portion 37 in a state that the non-contact vibrating portion is not in contact with the first vibrating section 31, but it is not limited to this example. For example, as a fourth modification shown in FIG. 18, in a first vibrating section 31, a groove-shaped portion 59 may be formed in place of the hollow portion 37. The groove-shaped portion 59 extends from a distal end of a first vibration main body portion 35 (a distal end of the first vibrating section 31) toward a proximal direction. Also in the present modification, a proximal side relay portion 36 is disposed at the distal end of the first vibrating section 31, and the distal end of the first vibrating section 31 becomes a first antinode position (a relay antinode position) A1 of a first vibration.

A non-contact vibrating portion 43 of a second vibrating section 32 extends in the groove-shaped portion 59. Also in the present modification, the non-contact vibrating portion 43 extends in a state that the non-contact vibrating portion is not in contact with the first vibrating section 31. In the second vibrating section 32, a distal side relay portion 42 is disposed at a middle position M different from second antinode positions A'1 to A'4 and second node positions N'1 to N'3 of a second vibration. The distal side relay portion 42 abuts on the proximal side relay portion 36. The non-contact vibrating portion 43 extends from the distal side relay portion 42 toward a proximal direction side.

According to the abovementioned configuration, similarly to the first embodiment, in the present modification, a magnitude V2c of a second amplitude at the second antinode positions A'1 to A'4 of the second vibration is larger than a magnitude V1 of a first amplitude at first antinode positions A1, A2 of the first vibration, when an ultrasonic probe 20 vibrates at a predetermined frequency f0.

Furthermore, as a fifth modification shown in FIG. 19, a horn portion 61 in which a sectional area perpendicular to a longitudinal axis C changes may be provided in a columnar portion 19. In the horn portion 61, the sectional area of the columnar portion 19 which is perpendicular to the longitudinal axis C decreases from a proximal direction toward a distal direction. The horn portion 61 is provided so that an amplitude of an ultrasonic vibration is enlarged in a part located to a distal direction side from the horn portion 61. Therefore, a magnitude V1 of a first amplitude at first antinode positions A1, A2 of the first vibrating section 31 becomes larger. In consequence, the amplitude of the ultrasonic vibration at a distal end of an ultrasonic probe 20 (a second vibrating section 32) is further effectively enlarged.

Furthermore, in the first embodiment, the ultrasonic vibrator 12 is attached to the columnar portion 19, but the present invention is not limited to this example. For example, as a sixth modification shown in FIG. 20, an ultrasonic vibrator 12 may be attached to a first vibrating section 31. Also in the present modification, an ultrasonic vibration generated in the ultrasonic vibrator 12 is transmitted to the first vibrating section 31.

In the present modification, a cylindrical member 62 to which the ultrasonic vibrator 12 is attached becomes the first vibrating section 31. Furthermore, a probe member 63 becomes a second vibrating section 32. An ultrasonic probe 20 is formed of the probe member 63. Similarly to the first embodiment, in the present modification, when an ultrasonic transmitting unit 3 vibrates at a predetermined frequency f0, a magnitude V2c of a second amplitude at second antinode positions A'1 to A'4 of a second vibration is larger than a magnitude V1 of a first amplitude at first antinode positions A1, A2 of a first vibration.

Furthermore, in the first embodiment, the first vibrating section 31 has two first antinode positions A1, A2 and one first node position N1, and the second vibrating section 32 has four second antinode positions A'1 to A'4 and three second node positions N'1 to N'3, but the numbers of the first antinode positions A1, A2, the first node position N1, the second antinode positions A'1 to A'4 and the second node positions N'1 to N'3 are not limited to those of this example. That is, in the first vibrating section 31, a distal end and a proximal end may become the first antinode positions (A1, A2) of the first vibration. Furthermore, in the second vibrating section, a distal end and a proximal end may become second antinode positions (A'1, A'4) of the second vibration. In consequence, the first vibrating section 31 and the second vibrating section 32, to which ultrasonic vibration is transmitted, vibrate at the predetermined frequency f0.

It is seen from the abovementioned modifications that the proximal side relay portion 36 may be provided in the first vibration main body portion 35 of the first vibrating section 31 and the proximal side relay portion 36 may be positioned at the relay antinode position A1 which is one of the first antinode positions (A1, A2) of the first vibration. Furthermore, in the second vibration main body portion 41 of the second vibrating section 32, the distal side relay portion 42 may be provided in a state that the distal side relay portion is continuous with the proximal side relay portion 36 of the first vibrating section 31 or abuts on the proximal side relay portion 36, and the distal side relay portion 42 may be positioned at the middle position M different from the second antinode positions (A'1 to A'4) and the second node positions (N'1 to N'3) of the second vibration. Furthermore, in the second vibrating section 32, the non-contact vibrating portion 43 in which the proximal end of the second vibrating section 32 is positioned may be provided, and the non-contact vibrating portion 43 may extend toward the proximal direction side from the distal side relay portion 42 in the state that the non-contact vibrating portion is not in contact with the first vibrating section 31. In consequence, when the ultrasonic transmitting unit 3 vibrates at the predetermined frequency f0, the magnitude V2c of the second amplitude of the second vibration at the second antinode positions (A'1 and A'2) of the second vibrating section 32 is larger than the magnitude V1 of the first amplitude of the first vibration at the first antinode positions (A1, A2) of the first vibrating section 31.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic transmitting unit comprising:
a first vibrating section which extends along a longitudinal axis, and which is configured to perform an ultrasonic vibration having more than one first antinode positions and a first node position at a predetermined frequency,
the first vibrating section including
a first vibration main body portion, and
a first relay portion provided in the first vibration main body portion, and positioned at a relay antinode position which is one of the first antinode positions when the first vibrating section vibrates at the predetermined frequency; and
a second vibrating section which is configured to perform a vibration having more than one second antinode positions and a second node position at the same predetermined frequency as in the first vibrating section when the ultrasonic vibration is transmitted from the first vibrating section,
the second vibrating section including
a second vibration main body portion,
a second relay portion which provided in the second vibration main body portion in a state that the second relay portion is continuous with the first relay portion of the first vibrating section or abuts on the first relay portion of the first vibrating section, and which is positioned at a middle position different from the second antinode positions and the second node position when the second vibrating section vibrates at the predetermined frequency, and
a non-contact vibrating portion in which an end portion of the second vibrating section is positioned and which extends from the second relay portion toward a first vibrating section side in a state that the non-contact vibrating portion is not in contact with the first vibrating section.

2. The ultrasonic transmitting unit according to claim 1, further comprising:
an ultrasonic vibrator which is configured to generate the ultrasonic vibration; and
a treatment portion which is configured to treat a treatment object by use of the ultrasonic vibration, wherein
the first vibrating section is configured to transmit the ultrasonic vibration transmitted from the ultrasonic vibrator toward a first transmitting direction,
the first relay portion is configured to transmit the ultrasonic vibration, transmitted through the first vibrating section, to the second vibrating section through the second relay portion,
the non-contact vibrating portion of the second vibrating section extends from the second relay portion toward a second transmitting direction side, when an opposite direction with respect to the first transmitting direction is the second transmitting direction, and
the treatment portion is provided in a first-transmitting-direction-side end portion of the second vibrating section.

3. The ultrasonic transmitting unit according to claim 2, wherein
the first vibrating section is configured to transmit the ultrasonic vibration toward the first transmitting direction to the first relay portion, and
the second vibrating section is configured to transmit the ultrasonic vibration, transmitted from the first relay portion through the second relay portion, toward the first transmitting direction to the treatment portion.

4. The ultrasonic transmitting unit according to claim 2, wherein
when an amplitude of the ultrasonic vibration in the first vibrating section is a first amplitude and an amplitude of the ultrasonic vibration in the second vibrating section is a second amplitude, the first amplitude at each of the first antinode positions has the same magnitude as the second amplitude at the middle position,
the vibration at the relay antinode position in the first vibrating section and the vibration at the middle position in the second vibrating section have the same phase with respect to each other, and
the second amplitude at each of the second antinode positions in the second vibrating section is larger than the first amplitude at each of the first antinode positions in the first vibrating section.

5. The ultrasonic transmitting unit according to claim 2, wherein
the second vibrating section has one end and the other end, and the non-contact vibrating portion forms the one end of the second vibrating section,
when it is defined that an n number is a natural number, the middle position of the second vibrating section is positioned between the n-th first-transmitting-direction-side second antinode position, which is one of the second antinode positions, and the n-th first-transmitting-direction-side second node position, and
the ultrasonic vibration of the second vibrating section at a most distal antinode position, which is one of the second antinode positions and is positioned at the other end of the second vibrating section, has the same phase as the ultrasonic vibration of the first vibrating section at the relay antinode position when the first vibrating section and the second vibrating section vibrate at the predetermined frequency.

6. The ultrasonic transmitting unit according to claim 2, wherein
the second vibrating section has one end and the other end, and the non-contact vibrating portion forms the one end of the second vibrating section,
when it is defined that an n number is a natural number, the middle position of the second vibrating section is positioned between the n-th first-transmitting-direction-side second node position and the (n+1)-th first-transmitting-direction-side second antinode position, which is one of the second antinode positions, and
the ultrasonic vibration of the second vibrating section at a most distal antinode position, which is one of the second antinode positions and is positioned at the other end of the second vibrating section, has an opposite phase with respect to the ultrasonic vibration of the first vibrating section at the relay antinode position when the first vibrating section and the second vibrating section vibrate at the predetermined frequency.

7. The ultrasonic transmitting unit according to claim 2, wherein the relay antinode position is positioned at a first-transmitting-direction-side end of the first vibrating section.

8. The ultrasonic transmitting unit according to claim 2, wherein
the first vibrating section has a distal portion and a proximal portion, and configured to transmit the ultrasonic vibration toward the first transmitting direction from a proximal portion side to a distal portion side,
the second vibrating section has a proximal portion and a distal portion in which the treatment portion is provided, and configured to transmit the ultrasonic vibration toward the first transmitting direction from the second relay portion to the distal portion, and the non-contact vibrating portion is positioned to a proximal portion side from the second relay portion.

9. The ultrasonic transmitting unit according to claim 1, wherein
a hollow portion is formed inside the first vibrating section, and
the non-contact vibrating portion of the second vibrating section is inserted into the hollow portion.

10. The ultrasonic transmitting unit according to claim 1, wherein a first axis parallel dimension along the longitudinal axis between the middle position and a nearby node position positioned closest to the middle position among the second node position in the second vibrating section is smaller than a second axis parallel dimension along the longitudinal axis between the middle position (M) and a nearby antinode position positioned closest to the middle position among the second antinode positions in the second vibrating section.

11. An ultrasonic transmitting unit which is formed by connecting a first transmitting member and a second transmitting member, the first transmitting member being configured to perform a vibration having more than one first antinode positions and a first node position at a predetermined frequency by an ultrasonic vibration, and the second transmitting member being configured to perform a vibration having more than one second antinode positions and a second node position at the same predetermined frequency as in the first transmitting member by the ultrasonic vibration,
wherein the first transmitting member includes:
a first vibration main body portion; and
a first relay portion provided in the first vibration main body portion, and positioned at a relay antinode position which is one of the first antinode positions in the first transmitting member when the first transmitting member vibrates at the predetermined frequency, and
the second transmitting member includes:
a second vibration main body portion;
a second relay portion which provided in the second vibration main body portion in a state that the second relay portion abuts on the first relay portion of the first transmitting member, and which is positioned at a middle position different from the second antinode positions and the second node position in the second transmitting member when the second transmitting member vibrates at the predetermined frequency; and
a non-contact vibrating portion in which an end portion of the second transmitting member is positioned and which extends from the second relay portion toward a first transmitting member side in a state that the non-contact vibrating portion is not in contact with the first transmitting member.

12. The ultrasonic transmitting unit according to claim 11, wherein
the first transmitting member is configured to transmit the ultrasonic vibration toward the first transmitting direction to the first relay portion, and
the second transmitting member has one end portion configured to treat a treatment object, and the second transmitting member is configured to transmit the ultrasonic vibration transmitted through the first relay portion and the second relay portion toward the first transmitting direction to the one end portion.

13. The ultrasonic transmitting unit according to claim 11, wherein
the first transmitting member has a distal portion and a proximal portion, and configured to transmit the ultrasonic vibration toward the first transmitting direction from the proximal portion to the distal portion,
the second transmitting member has a proximal portion and a distal portion configured to treat a treatment object, and the second transmitting member is configured to transmit the ultrasonic vibration toward the first transmitting direction from the second relay portion to the distal portion, and
the non-contact vibrating portion is positioned to a proximal portion side from the second relay portion.

* * * * *